US007695927B2

(12) United States Patent
Kim et al.

(10) Patent No.: US 7,695,927 B2
(45) Date of Patent: Apr. 13, 2010

(54) DETECTION OF HYPERTENSION USING GLUCURONIDATED METABOLIC PRODUCTS

(75) Inventors: Hyesook Kim, Bloomfield Hills, MI (US); Jorge H. Capdevila, Nashville, TN (US); Raymond R. Novak, Orchard Lake, MI (US); Deanna Kroetz, Burlingame, CA (US)

(73) Assignee: Detroit R & D, Bloomfield Hills, MI (US)

( * ) Notice: Subject to any disclaimer, the term of this patent is extended or adjusted under 35 U.S.C. 154(b) by 739 days.

(21) Appl. No.: 11/378,062

(22) Filed: Mar. 17, 2006

(65) Prior Publication Data

US 2006/0211064 A1 Sep. 21, 2006

Related U.S. Application Data

(60) Provisional application No. 60/663,554, filed on Mar. 18, 2005.

(51) Int. Cl.
*G01N 33/53* (2006.01)
*G01N 33/531* (2006.01)
*C12Q 1/48* (2006.01)
*G01N 33/532* (2006.01)
*C07K 16/00* (2006.01)

(52) U.S. Cl. .......................... 435/7.72; 435/7.1; 435/15; 436/544; 530/389.8

(58) Field of Classification Search .................. 435/7.1, 435/7.91, 7.93, 7.94; 436/815, 173; 530/388.9, 530/389.8
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,879,219 A | 11/1989 | Wands et al. | |
| 5,011,771 A | 4/1991 | Bellet et al. | |
| 5,281,521 A | 1/1994 | Trojanowski et al. | |
| 6,756,210 B2 * | 6/2004 | Hammock et al. ............. | 435/25 |

OTHER PUBLICATIONS

Capdevila, Jorge H. et al., "Cytochrome P450 and the Metabolism of Arachidonic Acid and Oxygenated Eicosanoids," *Cytochrome P450:* Structure Mechanism and Biochemistry (Ed. P.R. Ortiz de Montellano), 443-471 (1995).
Laethem, R.M. et al., "Identification of Rabbit Cytochromes P450 2C1 and 2C2 as Arachidonic Acid Epoxygenases," *Mol. Pharmacol.* 42, 958-963 (1992).
Daikh, B.E. et al., "Stereoselective Epoxidation of Arachidonic Acid by Cytochrome P-450s 2CAA and 2C2[1]," *J. Pharmacol.Exp. Ther.* 269, 1130-1135 (1994).
Zeldin, Darryl C. et al., "Molecular Cloning, Expression and Characterization of an Endogenous Human Cytochrome P450 Arachidonic Acid Epoxygenase Isoform[1]," *Arch. Biochem. Biophys.*, 322, 76-86 (1995).
Wu, Shu et al., "Molecular Cloning and Expression of CYP2J2, a Human Cytochrome P450 Arachidonic Acid Epoxygenase Highly Expressed in Heart," *Journal of Biological Chem.*, vol. 271, No. 7, 3460-3468 (1996).
Wu, Shu et al., "Molecular Cloning, Expression, and Functional Significance of a Cytochrome P450 Highly Expressed in Rat Heart Myocytes," *The Journal of Biological Chemistry*, vol. 272, No. 19, 12551-12559 (1997).
Kikuta, Yasushi et al., "A Novel Species of Cytochrome P-450 (P-45$_{ib}$) Specific for the Small Intestine of Rabbits," *The Journal of Biological Chemistry*, vol. 266, 17821-17825 (1991).
Makita, Keiko, et al., "Cytochrome P450, the arachidonic acid cascade, and hypertension: new vistas for an old enzyme system," *The FASEB Journal*, 1456-1463 (1996).
Capdevila, Jorge H. et al., "Cytochrome P-450 Arachidonic Acid Epoxygenase," *The Journal of Biological Chemistry*, vol. 267, No. 30, 21720-21726 (1992).
Omata, Ken et al., Age-related changes in renal cytochrome P-450 arachidonic acid metabolism in spontaneously hypertensive rats, *Am. J. Physiol.* 262, F8-F16 (1992).
Kroetz, Deanna L. et al., "Developmentally Regulated Expression of the CYO4A Genes in the Spontaneously Hypertensive Rat Kidney," *Molecular Pharmacology*, 52:362-372 (1997).
Newman, John W. et al., "The simultaneous quantification of cytochrome P450 dependent linoleate and arachidonate metabolics in urine by HPLC-MS/MS," *Journal of Lipid Res.* vol. 43:1563-1578 (2002).

(Continued)

*Primary Examiner*—Shafiqul Haq
(74) *Attorney, Agent, or Firm*—Kohn & Associates, PLLC

(57) ABSTRACT

A method to assess arachidonic acid (AA) metabolites-dependent hypertension by measuring glucuronidated dihydroxyeicosatrienoic acids (DHETs) and DHET metabolites in a biological sample which contains the epitopes unique to DHET (using any methods including GC/MS, LC/MS or ELISA) is disclosed. An example of the glucuronidated DHET metabolite is DHET-alcohols such as omega or omega-1 oxidated DHET and DHET esterified glycerol. The method further includes determining the amount of glucuronidated molecules containing a DHET-specific epitope which is immunoreactive with antibodies produced against DHETs. The present invention measuring glucuronidated DHET levels in a biological sample is useful for drug development and monitoring efficiency of drug treatment of a mammal who has AA epoxygenase-, epoxide hydrolase-and/or UDP-glucuronosyl transferase-dependent hypertension.

16 Claims, 3 Drawing Sheets

OTHER PUBLICATIONS

Huston, James S. et al., "Protein Engineering of Single-Chain Fv Analogs and Fusion Proteins," *Methods in Enzymology*, vol. 203, 46-88 (1991).

Johnson, Syd et al., "Construction of Single-Chain Fv Derivatives of Monoclonal Antibodies and Their Production in *Escherichia coli*," *Methods in Eznym*. vol. 203, 88-89 (1991).

Mernaugh and Mernaugh, "An Overview of Phage-Displayed Recombinant Antibodies," *Molec. Methods in Plant Path*. 359-365 (1995).

Harlow and Lane, Antibodies: A Laboratory Manual (1988).

Borrebaeck, Carl A.K., Antibody Engineering, A Practical Guide (1992).

Tijssen, P., "Practice and theory of enzyme immunoassays: Conjugation of haptens," vol. 15:279-296 (1987).

Yu, Zhigang, "Renal Cytochrome P450 Epoxygenases and Soluble Epoxide Hydrolase in Blood Pressure Regulation," Dissertation, Doctor of Philosophy in Pharmaceutical Chemistry in the Graduate Division of the Univ. of Calif. San Francisco (2004).

Glucuronidation of arachidonic and linoleic acid metabolites by human UDP-glucuronosyltransferases, David Turgeon, Sarah Chouinard, Patrick Belanger, Serge Picard, Hean-Francois Labbe, Pierre Borgeat and Alain Belanger, Journal of Lipid Research, vol. 44, (2003), pp. 1182-1191.

Metabolic Transformations of Leukotriene $B_4$ in Primary Cultures of Human Hepatocytes[1], Pat Wheelen, Joseph A. Hankin, Bahri bilir, Denis Guenette and Robert C. Murphy, Journal of Pharmacology and Experimental Therapeutics, vol. 288, No. 1, (1999), pp. 326-334.

\* cited by examiner

Fig. 1. A-B
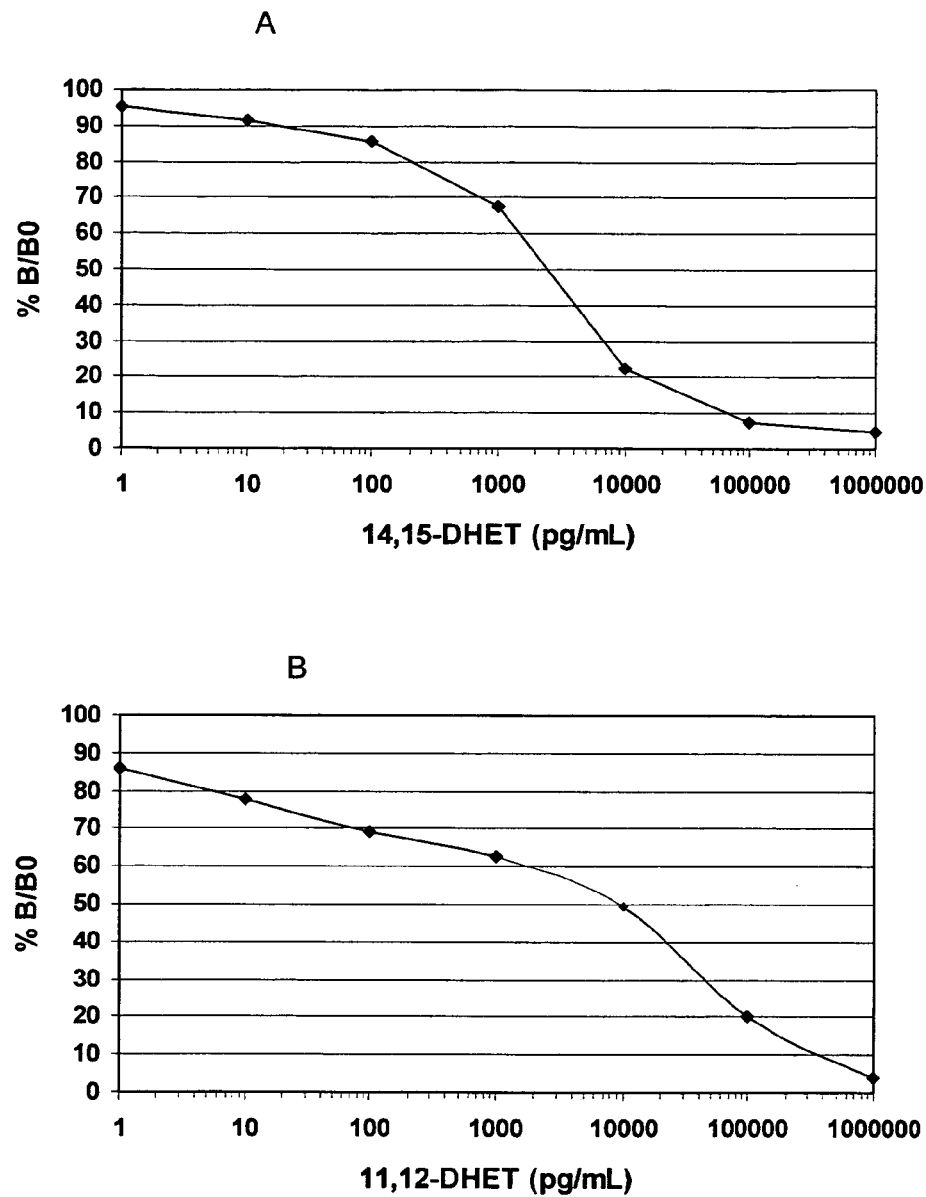

Fig. 2. A-B
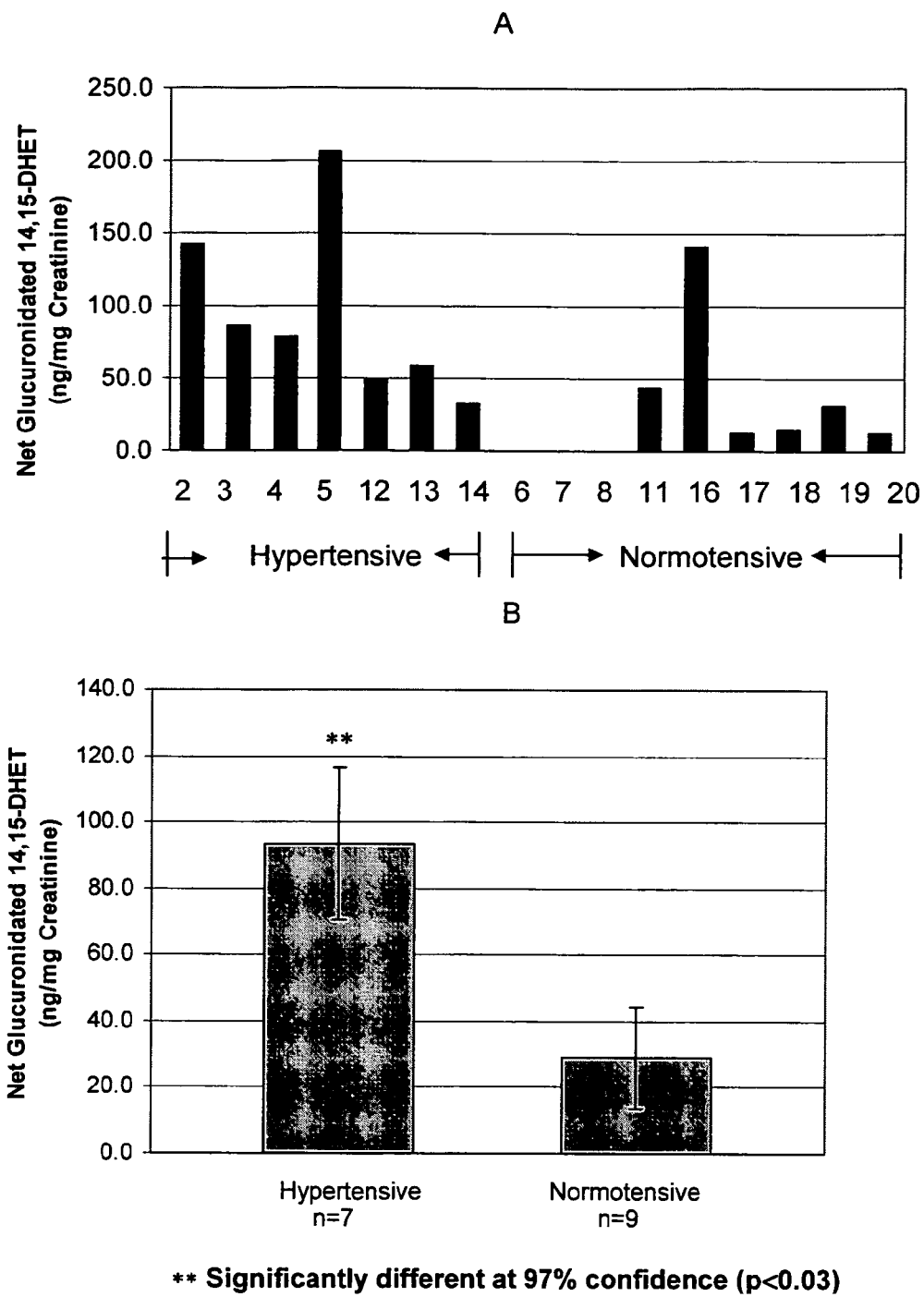
** Significantly different at 97% confidence (p<0.03)

Fig. 3. A-B
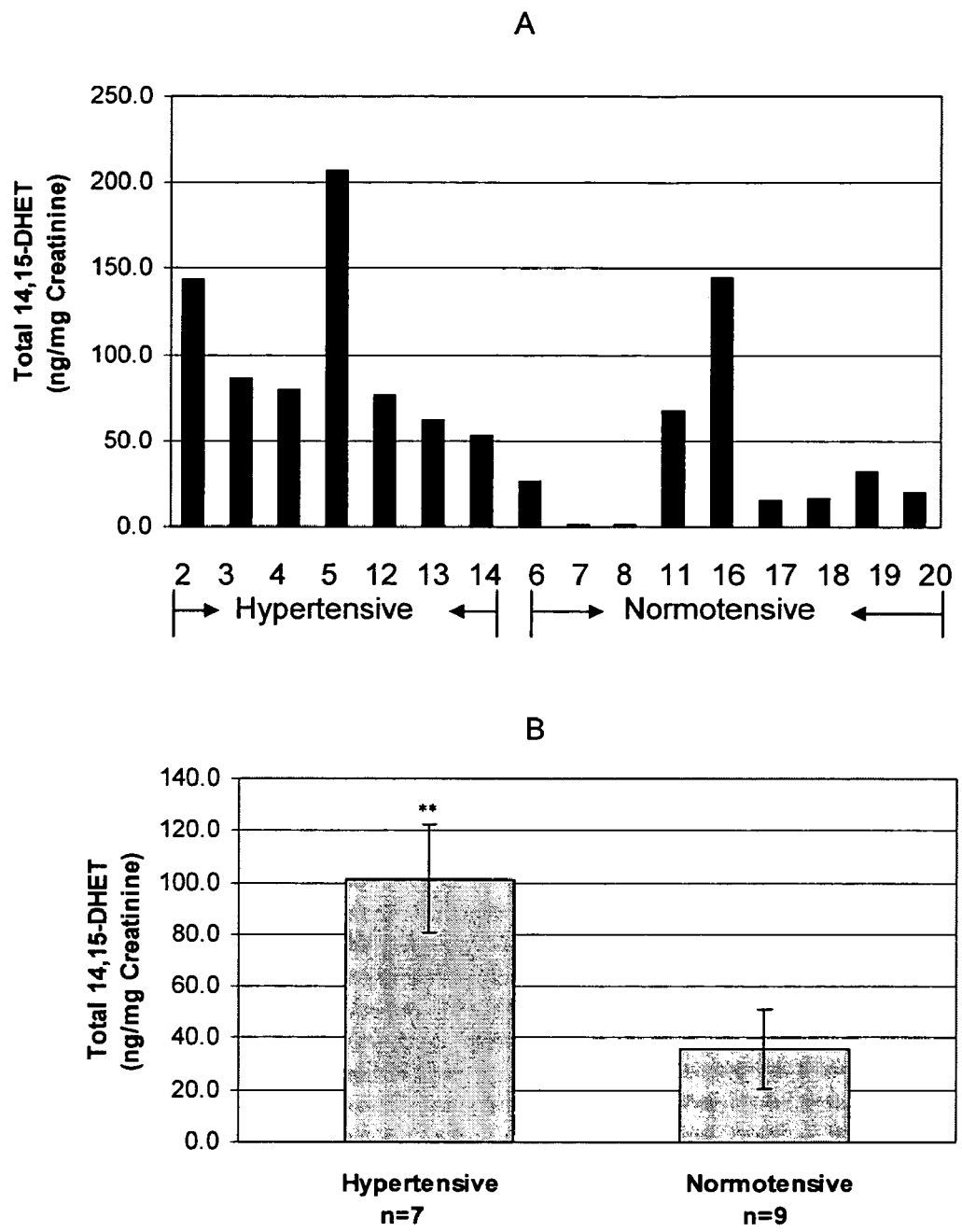
** Significantly different at 98% confidence (p<0.02)

DETECTION OF HYPERTENSION USING GLUCURONIDATED METABOLIC PRODUCTS

CROSSREFERENCE TO RELATED APPLICATIONS

This application claims benefit under 35 USC §119 (e) of U.S. Provisional Patent Application Ser. No. 60/663,554, filed Mar. 18, 2005.

BACKGROUND OF THE INVENTION

1. Field of the Invention

This invention relates to hypertension assessment and a method to screen hypertension drugs. In particular, the present invention relates to assessing hypertension based on arachidonic acid-derived metabolites. The present invention relates to measurement of glucuronidated DHET and glucuronidated DHET metabolites to monitor hypertension and development of drugs for arachidonic acid epoxygenase-, epoxide hydrolase- and UDP-glucuronosyl transferase-dependent hypertension.

2. Description of Related Art

Arachidonic acid ("AA") is a component of cellular membranes and plays a critical role as a mediator of cell and organ function through its metabolic cascade. The AA cascade includes prostaglandin synthases, lipoxygenases, and cytochromes P450 (CYPs). The CYP pathway is composed of lipoxygenases-like (allylic oxidation), $\overline{\omega}/\omega$-oxygenases and epoxygenases (olefin epoxidation), which metabolize M to produce 5-, 8-, 9-, 11-, 12-, and 15-hydroxyeicosatetraenoic acids (HETEs), 16- to 20-hydroxyeicosatetraenoic acids (OH-AAs), and 5,6-, 8,9-, 11,12- and 14,15-epoxyeicosatrienoic acids (EETs), respectively (1). Epoxide hydrolases hydrolyze biologically active EETs to their corresponding dihydroxyeicosatrienoic acids (DHETs) and UDP-glucuronosyl transferase transforms DHETs to glucuronidated DHETs.

CYPs which have been identified to be M epoxygenases are CYP2C11, CYP2C23, CYP2B1, and CYP2B2 expressed in rats (1), CYP2C1 and CYP2C2 expressed in rabbits (2,3), and CYP2C8 and CYP2C9/2C10 expressed in human (4). CYP2J is abundantly expressed in extrahepatic tissues (5-7).

EETs have potent vasoactive properties (vasodilator or vasoconstrictor). Urinary excretion of $Na^+$, EETs and DHETs decreased after inhibition of AA epoxygenase activity by treating rats with clotrimazole, which induced salt-sensitive and clotrimazole-dependent hypertension. A salt-sensitive phenotype of the Dahl rat was associated with a lack of increases in renal AA epoxygenases after intake of a high salt diet (8,9).

A spontaneous hypertensive rat (SHR) study indicated that ($\omega/\omega$-1 hydroxylase activity of kidney microsomes was significantly higher than that of normotensive Witstar Kyoto rats (WKY) whereas AA epoxygenase activity (EETs+DHETs) showed no difference between two strains at any age group tested (10). Thus, it was generally known that the developmental phase of hypertension was linked to increases in the activity of kidney microsomal $\omega/\omega$-1 hydroxylase. Indeed, recently the gene coding for CYP4A2 ($\omega/\omega$-1 hydroxylase) was found to be preferentially expressed in SHR (10,11).

However, the result obtained at the inventor's laboratory revealed that DHET levels in urine specimens obtained from SHR was ~56-fold higher than those of WKY (U.S. Pat. No. 6,534,282). The inventor also found that 14,15-DHET exists in the urine as free (ethyl acetate extractable) and conjugated (ethyl acetate unextractable) forms and antibodies produced against 14,15-DHETs recognize both free and several conjugated forms. Cross-reactivity of the antibodies with the conjugated form of 14,15- and 8,9-DHETs was further demonstrated by ELISAs using 14,15- and 8,9-DHETs conjugated to bovine serum albumin. Epoxide hydrolase activity may be measured by the ELISAs against 14,15-DHET. Anti-DHET does not recognize 14,15-EET (U.S. Pat. No. 6,534,282).

The specificity of the antibody developed against 14,15-DHET was further investigated utilizing slot blot analysis. The 14,15-DHET conjugated BSA, BSA alone and 8,9-DHET conjugated to BSA were blotted onto cellulose membrane. Slot blot analysis was carried out with anti-14,15-DHET. Though the same amount of protein is loaded to each lane (proteins were visualized by amido black staining), the antibody cross-reacted with 14,15-DHET conjugated BSA whereas the antibody failed to cross-react with 8,9-DHET which is structurally very similar to 14,15-DHET (U.S. Pat. No. 6,534,282).

Surprisingly, it is now noted that glucuronidated DHETs in a biological system can function as a biomarker for hypertension caused by increased activities of epoxide hydrolase- and UDP-glucuronosyl transferase. The AA metabolite-dependent hypertension drugs can be developed utilizing the glucuronidated marker.

SUMMARY OF THE INVENTION

According to the present invention, a method is disclosed to assess hypertension mediated by epoxide hydrolase- and UDP-glucuronosyl transferase by measuring glucuronidated DHETs and glucuronidated DHET metabolites in a biological sample which contains the epitopes unique to DHET (using any methods including mass spectrometry or immunoassay). An example of the DHET metabolite is a DHET shortened by β-oxidation, a DHET-alcohol such as an omega- or an omega-1-hydroxylated DHET and a DHET esterified glycerol.

The present invention includes a method of measuring glucuronidated DHET levels in a biological sample as a marker for hypertension useful for development of a drug for AA metabolite-dependent hypertension and monitoring the efficiency of drug treatment of a mammal who has the AA metabolite-dependent hypertension.

DESCRIPTION OF THE DRAWINGS

Other advantages of the present invention will be readily appreciated as the same becomes better understood by reference to the following detailed description when considered in connection with the accompanying drawings wherein:

FIGS. 1A-B are graphs showing typical standard curves obtained with various concentrations of 14,15-DHET (Panel A) and 11,12-DHET (Panel B). The DHET concentrations were ranged from 1 pg-100 ng/100 μL per well (10 pg-1 μg/mL).

FIGS. 2A-B are a graph showing levels of glucuronidated 14,15-DHET and 14,15-DHET metabolites in urine samples (Panel A) and a graph showing mean values with standard errors and statistical analysis of levels of glucuronidated 14,15-DHETs in urine samples (Panel B) obtained from 9 healthy and 7 hypertensive (preeclamptic) pregnant women.

FIGS. 3A-B is a graph showing levels of free and glucuronidated 14,15-DHETs and 14,15-DHET metabolites in urine samples (Panel A) and a graph showing mean values with standard errors and statistical analysis of levels of the total 14,15-DHETs in urine samples (Panel B) obtained from 9 healthy and 7 hypertensive (preeclamptic) pregnant women.

DETAILED DESCRIPTION OF THE INVENTION

According to the present invention, a method is disclosed to assess hypertension mediated by AA epoxygenase-, epoxide hydrolase- and UDP-glucuronosyl transferase by measuring the amount of free and glucuronidated DHETs and glucuronidated DHET metabolites, which are metabolites of AA epoxygenases (by this enzyme AA is biotransformed to EET), epoxide hydrolases (by this enzyme EET is biotransformed to DHET) and UDP-glucuronosyl transferase (by this enzyme DHET is biotransformed to glucuronidated DHET), in a biological sample which contains the glucuronidated DHETs. The method further includes determining the amount of glucuronidated molecules containing DHET-specific epitopes immunoreactive with antibodies produced against DHETs. The DHET-specific epitopes present in the sample are also measured after digestion of the sample with glucuronidase.

In general, a panel of healthy control samples is used that are within the normal range. The normal range is established as known in the art and is established for each assay method being utilized, e.g. GC/MS and immunoassays. Epoxide hydrolase- and UDP-glucuronosyl transferase-dependent hypertension is determined through the comparison wherein the amount of the glucuronidated DHETs is increased in the sample isolated from a hypertensive patient compared to controls. The increased glucuronidated DHET and glucuronidated DHET metabolites levels compared to the normal range are markers for a person at increased risk for hypertension.

The biological sample is generally selected from biological fluids which contain the glucuronidated DHETs and can include plasma, urine, cerebrospinal fluids, bile and joint fluids. Urine is the preferred sample.

It has been previously reported that M epoxygenase activities (EETs+DHETs) of kidney cortical microsomes obtained from spontaneously hypertensive rats (SHR) were not different from those of normotensive Wistar Kyoto rats (WKY) (10). However, the data obtained at the inventor's laboratory demonstrated that, when DHET levels in urine samples obtained from SHR were compared with those of WKY, contrary to the results obtained with kidney cortical microsome study of those rats in which EET+DHET levels were measured, urinary DHET levels of SHR were ~56-fold higher than those of WKY (U.S. Pat. No. 6,534,282). Thus, measurement of urinary DHET levels, not urinary EET+DHET levels, provides better assessment of hypertension mediated by AA epoxygenase and epoxide hydrolase.

The present invention is based on the finding that in addition to the AA epoxygenase and epoxide hydrolase, UDP-glucuronosyl transferase plays a critical role in hypertension mediated by AA metabolism. Glucuronidation of the DHETs is then a regulatory mechanism involved with essential and pregnancy-induced hypertensions.

As detailed in the experimental section below, sixteen coded human urine specimens were obtained and DHET and glucuronidated DHET levels were assayed. This was a blind test to remove any human biases on the treatment of the samples. Eventually, the identities of the urine specimens were revealed: they were urine specimens obtained from 7 hypertensive individuals (women with preeclampsia, pregnancy-induced hypertension) and 9 normotensive individuals (healthy pregnant women).

Glucuronidated 14,15-DHET levels in the urine samples obtained from women with preeclampsia and healthy pregnant women were measured using antibodies recognizing 14,15-DHET. The urine specimens were incubated with glucuronidase to cleave the glucuronic acid moiety attached to fatty acids. An increased level of immunoreactive 14,15-DHET epitope due to the cleavage (net glucuronidated 14,15-DHET epitope level) was obtained by subtracting the level of immunoreactive 14,15-DHET epitope of the urine sample at 0 time (as soon as glucuronidase was added) from the level obtained after 3 hours incubation of the samples. 14,15-DHET epitope levels of hypertensive urine samples were significantly different from normal urine samples (significantly different at 97% confidence, $p<0.03$) (FIG. 2, Tabel 1).

When the net glucuronidated epitope level was combined with the epitope level obtained without glucuronidase treatment (total 14,15-DHET epitope level), 14,15-DHET epitope levels of hypertensive urine samples were significantly different from normal urine samples (significantly different at 98% confidence, $p<0.02$) (FIG. 3, Tables 2 and 3). The result demonstrated that high glucuronidated 14,15-DHET levels are a marker for hypertension.

Per cents glucuronidated DHET of the samples were obtained by dividing the net glucuronidated 14,15-DHET epitope level with total 14,15-DHET epitope level (Table 3). Six out of sixteen samples had 99% and higher glucuronidation values. Nine samples had scattered values ranging from 0 (3 samples) to 60-70% (4 samples) and 80-95% (3 samples). Variations in glucuronation levels of the human urine samples were not expected because it has been previously reported that higher than 99% of detected diol residues in human urine were in a glucuronidated form (12). However, the experiment was based on only 2 human urine sample analyses (1 male and 1 female).

If the glucuronidation step of DHETs was not a rate-limiting step, all the DHET would have to be glucuronidated. Moreover, the rate of conversion of DHETs to glucuronidated DHETs should be much higher for the sample from the healthy group which had a low total DHET epitope level.

However, mean and SE values of % glucuronidated DHET for the healthy group were 55.6±14.6 which are lower than the hypertensive group (88.0±6.6) (significantly different at 91% confidence, $p<0.09$).

Thus, the results demonstrated that the AA metabolites-dependent hypertension was caused by not only epoxide hydrolase activity alone but also by UDP-glucuronosyl transferse activity. DHETs may activate the peroxisome proliferator-activated receptor (PPAR) which has been reported to increase UDP-glucuronosyl transferase expression. The 14,15-DHET epitope can be from 14,15-DHET as well as fatty acids shortened by beta-oxidation, fatty acids derived from fatty acids containing 18 carbons, omega-3 AA, fatty acids further oxidated form of 14,15-DHET including an omega- or an omega-1 hydroxylated 14,15-DHET and 14,15-DHET esterified with a molecule via a carboxyl group of the DHET, e.g. DHET esterified to glycerol.

In general, the quantification of the sample is done utilizing an immunoassay as described in the Examples herein. However, alternative methods such as GC/MS or HPLC can be used. Most of the techniques used in performing immunoassays are widely practiced in the art, and most practitioners are familiar with the standard resource materials which describe specific conditions and procedures. However, for convenience, the following paragraph may serve as a guideline.

In general, ELISAs are the preferred immunoassays employed to assess the amount of DHETs with and without pre-cleavage of the glucuronic acid moiety of the glucuronidated DHET in a specimen. ELISA assays are well known to those skilled in the art. Polyclonal, monoclonal and recombinant antibodies can be used in the assays. Where appropriate other immunoassays, such as radioimmunoassays (RIAs) or fluoroimmunoassays (FIAs) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 and may be adapted to be used the method of the present invention.

Free DHETs, glucuronidated DHETs and glucuronidated DHET metabolites are measured utilizing the immunoassay as set forth for example in the Examples herein with an antibody which recognized DHETs and metabolized DHETs after digestion of the glucuronic acid moiety of the glucuronidated DHETs with glucuronidase. Alternatively, antibodies can be utilized which are specific for each form. Such antibodies can be produced as described herein and tested as set forth in Example 1.

Most of the techniques used to produce antibodies are widely practiced in the art, and most practitioners are familiar with the standard resource materials which describe specific conditions and procedures. However, for convenience, the following paragraphs may serve as a guideline.

Antibody production: Antibodies (immunoglobulins) may be either monoclonal or polyclonal and are raised against the immunogen. Such immunogens can be used to produce antibodies by standard antibody production technology well known to those skilled in the art as described generally in Harlow and Lane, Antibodies: A laboratory Manual, Cold Spring Harbor Laboratory, Cold Spring Harbor, N.Y., 1988 and Borrebaeck, Antibody Engineering—A practical Guide, W. H. Freeman and Co., 1992. Antibody fragments may also be prepared from the antibodies and include Fab, F(ab')$_2$, and Fv by methods known to those skilled in the art.

For producing polyclonal antibodies a host, such as a rabbit or goat, is immunized with the immunogen, generally together with an adjuvant and, if necessary, coupled to a carrier: antibodies to the immunogen are collected from the sera. Further, the polyclonal antibody can be absorbed such that it is monospecific. That is, the sera can be absorbed against related immunogens, e.g. the free and conjugated forms of EETs and DHETs, so that no cross-reactive antibodies remain in the sera thereby rendering it monospecific. Testing for this specificity can be undertaken as described in Example 1.

For producing monoclonal antibodies the technique involves hyperimmunization of an appropriate donor with the immunogen or immunogen fragment, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (13-15), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody.

The antibody or antibody fragment can be bound to a solid support substrate or conjugated with a detectable moiety or be both bound and conjugated as is well known in the art to be used in the immunoassay (16). The binding of antibodies to a solid support substrate is also well known in the art (17,18). The detectable moieties contemplated with the present invention can include ferritin, alkaline phosphatase, β-galactosidase, peroxidase, urease, fluorescein, rhodamine, tritium, $^{14}$C and iodination as needed for the immunoassay.

The above discussion provides a factual basis for the method of the present invention to measure glucuronidated DHET levels including free DHETs, glucuronidated DHETs and metabolites of DHETs as a profile of hypertension of an individual. The elevated glucuronidated DHET levels in a biological sample are a useful tool to develop a hypertension drug and monitor efficiency of the drug treatment. The methods used with and the utility of the present invention can be shown by the following non-limiting examples and accompanying figures.

EXAMPLES

Materials and Methods

Materials

DHETs (higher than 98% pure by HPLC and GC/MS) were provided by laboratories of Drs. Jorge H. Capdevila and John R. Falck. The 14,15- and 11,12-DHET ELISA kits were produced at Detroit R&D. Other reagents were obtained from Sigma Chemical Co.

Antibody Production

Synthetic 14,15- or 11,12-DHETs were coupled to KLH as previously described (19). The conjugate was used to immunize a goat and antibody titers were determined by ELISA using DHET-conjugated bovine serum albumin (BSA).

Purification of IgG Fraction of Antisera

IgG fractions of antibody prepared against 14,15- or 11,12-DHET were purified from sera using protein-G affinity chromatography (Pierce Co.). The IgG bound to the protein G column was eluted with 50 mM glycine-HCl buffer, pH 2.5, and immediately neutralized with 0.5 M tris-HCl, pH 7.6. This procedure did not affect the specificity of the antibodies.

Human Urine Collection

Collection and storage of urine samples from 9 healthy and 7 hypertensive (preeclamptic) pregnant women were carried out as previously described in Zhigang Yu's Ph.D. thesis (20). Urinary creatinine levels were determined by the clinical laboratory at University of California, San Franscisco.

Glucuronidated 14,15-DHET Analysis

Glucuronidase treatment was carried out as described by Newman et al. (12). Urine samples were diluted with TBS. Glucuronidase dissolved in 1 M sodium citrate (pH 5.5) was added after 5 minutes preincubation of the urine samples at 37° C. The samples (5-fold dilution) were taken as soon as the glucuronidase is added (0 hour digestion) and at 3 hours after addition of the glucuronidase (3 hours digestion) and immediately frozen in dry ice. Alternatively, glucuronidase digestion can be terminated by addition of a commercially available glucuronidase inhibitor. ELISA was carried out after neutralizing and further diluting the sample with TBS and 14,15-DHET HRP-conjugate dilution buffer. Net glucuronidated DHET levels were calculated by subtracting the 14,15-DHET level obtained with 0 hour sample from the 14,15-DHET level obtained from 3 hours digested sample. Free DHET levels were obtained by ELISA using 4-fold diluted urine samples.

Solid Phase Competitive Enzyme-Linked Immunosorbent Assay (ELISA)

High-binding microplates were coated with protein G-purified IgG suspended in 1 M carbonate, pH 9.0, (10 μg/well; 200 μL/well final volume) and then covered with parafilm. After overnight incubation at room temperature, the wells were gently washed five times with tris buffered saline (TBS), pH 7.5, containing 0.1% tween. Non-specific sites were blocked by the addition of 0.2 mL of 5% (w/v) nonfat dry milk in TBS. After 2 hours of incubation at room temperature, they were washed three times with TBS-tween.

Samples obtained with and without glucuronidase pretreatment were 4-5-fold diluted with TBS (100 μL). The diluted samples and standards (100 μL) were added to the IgG-coated plate. Approximately 50 ng of the DHET-HRP conjugates were diluted with DHET HRP-dilution buffer (100 μL) and added to the well. Following incubation for 2 hours to permit competitive binding of the molecules to the antibody, unbound material was removed by thorough washing of the wells with TBS-tween, and 150 μL of a colorimetric substrate for HRP [3,3',5,5' tetramethylbenzidine (TMB) and hydrogen peroxide] (Sigma Co.) was added. The plate is then incubated for 30 minutes, the reaction stopped by addition of 75 μL of 1 N $H_2SO_4$, and the absorbance at 450 nm was measured using a microtiter plate reader. Under these assay conditions, the amount of color in a well is inversely proportional to the initial concentration of the sample or the standard ligand.

Statistics

Statistical analysis was carried out using Statview 512 software (Brain Power, Inc., Calabasas, Calif.) and significance between groups was analyzed using one factor anova (Scheffe F-test).

EXAMPLE 1

Development of the Immunoassay

Sensitivity of Antibodies Produced Against 14,15-DHET and 11.12-DHET

Goats were immunized with 14,15-DHET and 11,12-DHET KLH conjugates. The goat anti-sera recognized BSA conjugated with 14,15-DHET and 11,12-DHET, respectively, whereas preimmune sera of the goats failed to recognize 14,15-DHET or 11,12-DHET conjugated to BSA. A typical standard graph for 14,15-DHET (Panel A) and 11,12-DHET (Panel B) are presented in FIG. 1. The detection limits for 14,15-DHET and 11,12-DHET with ELISA were ~1 pg or 10 pg/mL as the standard was added in 100 μL to each well.

Specificity of Antibodies for 14,15-DHET and 11,12-DHET

The specificity of the 14,15-DHET ELISA was investigated using authentic DHET and a panel of eicosanoids which, based on their structure, might be anticipated to compete with 14,15-DHET for binding to antibodies against 14,15-DHET. Anti-14,15-DHET did not cross-react with 5,6-, 8,9-, 11,12- or 14,15-EET, 5,6-DHET, 15(S)HETE, 5(s) 15(S)DiHETE, arachidonic acid, Thromboxane $B_2$, $PGE_2$, $PGF_{2\alpha}$ or 6-keto-$PGF_{1\alpha}$. There was a slight cross-reaction with 8,9- and 11,12-DHET (3.3% for both). These result demonstrated that generally anti-DHET does not recognize EETs because the diol epitope of DHET is drastically different from the epoxide epitope of EET.

Anti-11,12-DHET did not cross-react with 5(s)15(S)Di-HETE and arachidonic acid as expected from the 14,15-DHET specificity result. There was a slight cross-reactivity with 8,9-DHET and 14,15-DHET.

EXAMPLE 2

Levels of Free and Glucuronidated 14,15-DHET and Glucuronidated 14,15-Metabolites in Human Urine Specimens obtained from Healthy and Hypertensive (Preeclamptic) Pregnant Women.

Urine samples obtained from 7 preeclamtic and 9 healthy women were incubated with glucuronidase (Sigma Co.) to cleave glucuronic acid moeity attached to fatty acids as previously described (12). An increased level of immunoreactive 14,15-DHET epitope by the glucuronidase cleavage (net glucuronidated 14,15-DHET epitope level) was obtained by subtracting the level of immunoreactive 14,15-DHET epitope of the urine sample at 0 time (as soon as glucuronidase was added) from the level obtained at 3 hours incubation (Table 1, FIG. 2). Specifically, urine samples were treated with glucuronidase for 3 hours at 37° C. in sodium citrate (pH 5.5) followed by ELISA analyses. Aliquots of urine samples were also obtained for ELISA analysis as soon as glucuronidase is added (0 hour digestion). After ELISA, the value at 0 hour digestion was subtracted from the value at 3 hours digestion to obtain the net glucuronidated DHET epitope value.

ELISA was carried out using horseradish peroxidase system and the bound enzyme conjugate was detected by the addition of 3,3'5,5'-tetra-methylbenzidine (TMB). Reaction was stopped with an acid stop solution and read at 450 nm. Optical density at 450 nm was converted to B/Bo×100. B denotes absorbance at 450 nm and Bo denotes the maximum absorbance reading obtained in the absence of 14,15-DHET.

The 14,15-DHET epitope levels without glucuronidase cleavage were measured (Table 2) and added to the net glucuronidated 14,15-DHET epitope levels to obtain total 14,15-DHET epitope levels in each urine sample (Table 3, FIG. 3). For 14,15-DHET epitope measurement without glucuronidase treatment, urine samples were diluted 4-fold with TBS and ELISA was carried out using horseradish peroxidase system and the bound enzyme conjugate was detected by the addition of 3,3'5,5'-tetra-methylbenzidine (TMB). Reaction was stopped with an acid stop solution and read at 450 nm. Optical density at 450 nm was converted to B/Bo×100. B denotes absorbance at 450 nm and Bo denotes the maximum absorbance reading obtained in the absence of 14,15-DHET.

The 16 urine samples with standards were analyzed by 14,15-DHET ELISA in quadruplicate. The mean optical density (OD) of each sample and % B/Bo was obtained. 14,15-DHET levels of the samples were determined using results obtained with various concentrations of 14,15-DHET standards. The value is multiplied by a dilution factor and divided by creatinine level of each urine sample.

Net glucuronidated DHET epitope levels were higher than free DHET levels except for 3 samples (Table 3). Contrary to the previous report that higher than 99% of urinary DHET was in a glucuronidated form (12), only 4 out of 16 samples contained the glucuronidated form higher than 99% of total 14,15-DHET epitopes. Moreover, glucuronidation levels of the samples varied ranging from 0 to 100% (Table 3). This result demonstrated that UDP-glucuronosyl transferase which transforms DHET to a bulkier and more charged molecule plays a critical role in hypertension.

The net glucuronidated 14,15-DHET epitope levels of hypertensive urine samples were significantly different from normal urine samples (at 97% confidence, $p<0.03$) (FIG. 2, Table 1). When the net glucuronidated epitope level was combined with the epitope level obtained without glucuronidase treatment (total 14,15-DHET epitope level), 14,15-DHET epitope levels of hypertensive urine samples were significantly different from normal urine samples (at 98% confidence, $p<0.02$) (FIG. 3, Table 3). Thus, when the free 14,15-DHET epitope value was added to glucuronidated 14,15-DHET epitope value, significance of difference between hypertensive and normal urine sample increased by 1%.

Through out this application, various publications, including Unite States patents, are referenced by author and year and patents by number. Full citations for the publications are listed below. The disclosures of these publications and patents in their entireties are hereby incorporated by reference into this application in order to more fully describe the state of the art to which this invention pertains. The invention has been used is intended to be in the nature of words of description rather than of limitation.

Obviously, many modifications and variations of the present invention are possible in the light of the above teachings. It is, therefore, to be understood that within the scope of the appended claims, the invention may be practiced otherwise than as specifically described.

TABLE 2

Levels of 14,15-DHET epitopes in urine specimens obtained from healthy and hypertensive (preeclamptic) pregnant women without glucuronidase treatment.

| Urine Specimen | | OD | % B/Bo | ng/250 uL | ng/mL |
|---|---|---|---|---|---|
| Hypertensive | 2 | 0.65 | 79 | 0.40 | 1.60 |
| | 3 | 0.65 | 80 | 0.12 | 0.48 |
| | 4 | 0.73 | 94 | 0.04 | 0.16 |
| | 5 | 0.76 | 98 | 0.03 | 0.10 |
| | 12 | 0.45 | 50 | 10.40 | 41.60 |
| | 13 | 0.57 | 68 | 1.20 | 4.80 |
| | 14 | 0.55 | 65 | 4.00 | 16.00 |
| Healthy | 6 | 0.44 | 47 | 10.01 | 40.03 |
| | 7 | 0.74 | 95 | 0.05 | 0.18 |
| | 8 | 0.66 | 82 | 0.11 | 0.43 |
| | 11 | 0.50 | 57 | 7.00 | 28.00 |
| | 16 | 0.72 | 90 | 0.05 | 0.20 |
| | 17 | 0.58 | 69 | 1.10 | 4.40 |
| | 18 | 0.57 | 68 | 1.20 | 4.80 |
| | 19 | 0.64 | 80 | 0.12 | 0.48 |
| | 20 | 0.64 | 79 | 0.40 | 1.60 |

TABLE 1

Levels of net glucuronidated 14,15-DHET epitopes in urine specimens obtained from healthy and hypertensive (preeclamptic) pregnant women.

| Urine Specimen | | 3 hour | | | | 0 hour | | | | Net Glucuronidated DHET |
|---|---|---|---|---|---|---|---|---|---|---|
| | | OD | % B/Bo | ng/200 uL | ng/mL | OD | % B/Bo | ng/200 uL | ng/mL | ng/mL |
| Hypertensive | 2 | 0.20 | 23 | 70 | 350 | 0.24 | 29 | 45.0 | 225.0 | 125.0 |
| | 3 | 0.27 | 36 | 40 | 200 | 0.29 | 39 | 25.0 | 125.0 | 75.0 |
| | 4 | 0.40 | 60 | 8 | 40 | 0.44 | 67 | 5.0 | 25.0 | 15.0 |
| | 5 | 0.29 | 39 | 30 | 150 | 0.37 | 55 | 11.0 | 55.0 | 95.0 |
| | 12 | 0.18 | 19 | 80 | 400 | 0.21 | 24 | 65.0 | 325.0 | 75.0 |
| | 13 | 0.23 | 27 | 50 | 250 | 0.26 | 34 | 35.0 | 175.0 | 75.0 |
| | 14 | 0.23 | 28 | 45 | 225 | 0.24 | 30 | 40.0 | 200.0 | 25.0 |
| Healthy | 6 | 0.17 | 16 | 90 | 450 | 0.18 | 19 | 90.0 | 450.0 | 0.0 |
| | 7 | 0.33 | 47 | 11 | 54 | 0.32 | 46 | 10.8 | 54.0 | 0.0 |
| | 8 | 0.30 | 42 | 23 | 115 | 0.30 | 41 | 23.0 | 115.0 | 0.0 |
| | 11 | 0.20 | 23 | 70 | 350 | 0.21 | 25 | 60.0 | 300.0 | 50.0 |
| | 16 | 0.22 | 27 | 50 | 250 | 0.24 | 31 | 35.0 | 175.0 | 75.0 |
| | 17 | 0.15 | 14 | 100 | 500 | 0.18 | 18 | 95.0 | 475.0 | 25.0 |
| | 18 | 0.21 | 24 | 60 | 300 | 0.23 | 28 | 50.0 | 250.0 | 50.0 |
| | 19 | 0.25 | 31 | 40 | 200 | 0.28 | 37 | 30.0 | 150.0 | 50.0 |
| | 20 | 0.46 | 71 | 4 | 20 | 0.48 | 76 | 3.5 | 17.5 | 2.5 |

TABLE 3

Levels of total 14,15-DHET epitopes in urine specimens obtained from healthy and hypertensive (preeclamptic) pregnant women and % glucuronidated form in each urine specimen.

| Urine Specimen | | Net Glucuronidated DHET ng/mL (A) | Free DHET ng/mL (B) | Total ng/mL (A + B) | Creatinine mg/mL (C) | ng/mg Creatinine | | | % Glucuronidated form |
| --- | --- | --- | --- | --- | --- | --- | --- | --- | --- |
| | | | | | | Net Glucuronidated DHET (A/C) | Free DHET (B/C) | Total (A + B)/C | |
| Hyper- | 2 | 125.0 | 1.60 | 126.60 | 0.88 | 142.05 | 1.82 | 143.86 | 98.74 |
| tensive | 3 | 75.0 | 0.48 | 75.48 | 0.87 | 86.21 | 0.55 | 86.76 | 99.36 |
| | 4 | 15.0 | 0.16 | 15.16 | 0.19 | 78.95 | 0.84 | 79.79 | 98.94 |
| | 5 | 95.0 | 0.10 | 95.10 | 0.46 | 206.52 | 0.22 | 206.74 | 99.89 |
| | 12 | 75.0 | 41.60 | 116.60 | 1.52 | 49.34 | 27.37 | 76.71 | 64.32 |
| | 13 | 75.0 | 4.80 | 79.80 | 1.28 | 58.59 | 3.75 | 62.34 | 93.98 |
| | 14 | 25.0 | 16.00 | 41.00 | 0.77 | 32.47 | 20.78 | 53.25 | 60.98 |
| Healthy | 6 | 0.0 | 40.03 | 40.03 | 1.53 | 0.00 | 26.16 | 26.16 | 0.00 |
| | 7 | 0.0 | 0.18 | 0.18 | 0.27 | 0.00 | 0.67 | 0.67 | 0.00 |
| | 8 | 0.0 | 0.43 | 0.43 | 0.44 | 0.00 | 0.98 | 0.98 | 0.00 |
| | 11 | 50.0 | 28.00 | 78.00 | 1.15 | 43.48 | 24.35 | 67.83 | 64.10 |
| | 16 | 75.0 | 0.20 | 75.20 | 0.52 | 144.23 | 0.38 | 144.62 | 99.73 |
| | 17 | 25.0 | 4.40 | 29.40 | 1.94 | 12.89 | 2.27 | 15.15 | 85.03 |
| | 18 | 50.0 | 4.80 | 54.80 | 3.28 | 15.24 | 1.46 | 16.71 | 91.24 |
| | 19 | 50.0 | 0.48 | 50.48 | 1.59 | 31.45 | 0.30 | 31.75 | 99.05 |
| | 20 | 2.5 | 1.60 | 4.10 | 0.21 | 11.90 | 7.62 | 19.52 | 60.98 |

REFERENCES

1. Capdevila, J. H., Zeldin, D., Makita, K., Karara, A., and Falck, J. R. (1995) in Cytochrome P450: Structure, Mechanism, and Biochemistry (Ed. P. R. Ortiz de Montellano) pp. 443-471, Plenum, New York, N.Y.
2. Laethem, R. M., and Koop, D. R. (1992) Mol. Parmacol. 42, 958-963.
3. Daikh, B. E., Laethem, R. M., and Koop, D. R. (1994) J. Pharmacol. Exp. Ther. 269, 1130-1135.
4. Zeldin, D. C., DuBois, R. N., Faick, J. R., and Capdevila, J. H. (1995) Arch. Biochem. Biophys. 322, 76-86.
5. Wu, S., Moomaw, C. R., Tomer, K. B., Falck, J. R. and Zeldin, D. C. (1996) J. Biol. Chem. 271, 3460-3468.
6. Wu, S., Chen, W., Murphy, E., Gabel, S., Tomer, K. B., Foley, J., Steenbergen, C., Falck, J. R., Moormaw, C. R. and Zeldin, D. C. (1996) J. Biol. Chem. 272, 12551-12559.
7. Kikuta, Y., Sogawa, K., Haniu, M., Kinosaki, M., Kusunose, E., Nojima, Y., Yamamoto, S., Ichihara, K., Kusunose, M. and Fujii-Kuriyama, Y. (1991) J. Biol. Chem. 266, 17821-17825.
8. Makita, K., Falck, J. R., and Capdevila, J. H. (1996) FASEB J. 10,1456-1463.
9. Capdevila, J. H., Wei, S., Yan, J., Karara, A., Jacobson, J. R., Falck, J. R., Guengerich, F. P., and DuBois, R. N. (1992) J. Biol. Chem. 267, 21720-21726.
10. Omata, K., Abraham, N. G., Escalante, B. and Schwartzman, M. L. (1992) Am. J. Physiol. 262, F8-F16.
11. Kroetz, D. L., Huse, L. M., Thuresson, A. and Grillo, M. P. (1997) Mol. Pharmacol. 52, 362-372.
12. Newman, J. W., Watanabe, T. and Hammock, B. D. (2002) J. Lipid Res. 43,1563-1578.
13. Huston et al., 1991 "Protein Engineering of Single-Chain Fv Analogs And Fusion Proteins" in Methods in Enzymology (J J Langone, ed.; Academic Press, New York, N.Y.) 203:46-88.
14. Johnson and Bird, 1991, "Construction of Single-Chain Fvb Derivatives of Monoclonal Antibodies and Their Production in *Escherichia coli* in Methods in Enzymology (J J Langone, ed.; Academic Press, New York, N.Y.) 203:88-89.
15. Mernaugh and Menaugh, 1995, "An Overview of Phage-Displayed Recombinant Antibodies" in Molecular Methods in Plant Pathology (RP Singh and US Singh, eds.; CRC Press Inc., Boca Raton, Fla.) pp. 359-365.
16. Johnstone & Thorpe, Immunochemistry in Practice, Blackwell Scientific Publications, Oxford, 1982.
17. Harlow and Lane, Antibodies: A laboratory Manual, Cold Spring Harbor Laboratory, Cold Spring Harbor, N.Y., 1988.
18. Borrebaeck, Antibody Engineering—A practical Guide, W. H. Freeman and Co., 1992.
19. Tijssen, P. (1987) Conjugation of Haptens in Laboratory Techniques in Biochemistry and Molecular Biology (Eds. R. H. Burdon and P. H. van Knippenberg) Vol. 15 Practice and Theory of Enzyme Immunoassays. Pp. 279-296. Elsevier, New York, N.Y.
20. Yu, Zhigang (2004) Thesis deposited in the library at University of California, San Francisco.

The invention claimed is:

1. A method for assessing the presence of hypertension in a mammal comprising the steps of measuring an amount of glucuronidated dihydroxyeicosatrienoic acids (DHETs) from a test sample from a mammal; comparing the amount of glucuronidated dihydroxyeicosatrienoic acids in the test sample to a control sample from a non-hypertension mammal of a same species and determining if the test sample contains a comparatively elevated amount of the glucuronidated DHETs as an indication of hypertension mediated by one or both of epoxide hydrolase and UDP-glucuronosyl transferase; wherein the test sample is selected from the group consisting of urine, blood, liver and kidney.

2. The method as defined in claim 1, wherein said measuring an amount of glucuronidated dihydroxyeicosatrienoic acids includes the steps of:
   obtaining a test specimen from said test sample;
   adding glucuronidase to the test specimen;
   collecting a first sample from the test specimen at time zero of glucuronidase digestion, and a second sample after digestion is completed
   immunoassaying the first and second samples with antibody immunoreactive with a specific DHET; and determining the net amount of the specific DHET that is glurcuronidated by subtracting the amount of immunoreactive DHET in the first sample from the amount of immunoreactive DHET in the second sample.

3. The method as defined in claim 2, wherein said antibodies are immunoreactive with 14,15-DHETs.

4. The method as defined in claim 1, further including the step of identifying patients with hypertension.

5. The method as defined in claim 4, wherein said patient is a pregnant woman.

6. The method as defined in claim 5, wherein said patient has pregnancy-induced hypertension.

7. The method as defined in claim 1, wherein said test sample is in a urine sample.

8. The method as defined in claim 1, wherein said measuring step is further defined as measuring glucuronidated DHET metabolites.

9. The method as defined in claim 8, wherein said measuring of glucuronidated DHET metabolites includes the steps of:
  obtaining a test specimen from said test sample;
  adding glucuronidase to the test specimen;
  collecting a first sample from the test specimen at time zero of glucuronidase digestion, and a second sample after digestion is completed
  immunoassaying the first and second samples with antibody immunoreactive with a specific DHET metabolite; and
  determining the net amount of the specific DHET metabolite that is glurcuronidated by subtracting the amount of immunoreactive DHET metabolite in the first sample from the amount of immunoreactive DHET metabolite in the second sample.

10. The method as defined in claim 9, wherein said antibodies are immunoreactive with metabolites of 14,15-DHET.

11. A method for determining DHET-dependent UDP-glycuronosyl transferase activity in a biological system including the steps of:
  converting a known amount of a DHET to the corresponding glucuronidated DHET by UDP-glycuronosyl transferase activity in a biological system;
  collecting a first sample and a second sample;
  adding glucuronidase to the first sample and allowing complete digestion;
  leaving untreated the second sample;
  immunoassaying the first sample and the second sample with antibody immunoreactive with a specific DHET;
  determining the net amount of the specific DHET that is glurcuronidated by subtracting the amount of immunoreactive DHET in the first sample from the amount of immunoreactive DHET in the second sample; and
  determining DHET-dependent UDP-glururonosyl transferase activity.

12. The method as defined in claim 11, wherein said antibody immunoreactive with a specific DHET is immunoreactive with a DHET selected from the group comprising 5,6-DHET, 8,9-DHET, 14,15-DHET, and 11,12-DHET.

13. The method as defined in claim 1, wherein said measuring an amount of glucuronidated dihydroxyeicosatrienoic acids includes the steps of:
  obtaining a test specimen from said test sample;
  immunoassaying a first sample of the test specimen with an antibody immunoreactive with the glucuronidated form of a specific DHET;
  immunoassaying a second sample of the test specimen with an antibody immunoreactive with the free form of the specific DHET; and
  determining the total (free+glucuronidated) amount of the specific DHET by adding the amount of immunoreactive glucuronidated DHET in the first sample to the amount of immunoreactive free DHET in the second sample.

14. The method as defined in claim 13 wherein the antibody immunoreactive with the glucuronidated form of a specific DHET is an antibody immunoreactive with the glucuronidated form of a DHET selected from the group comprising 5,6-DHET, 8,9-DHET, 14,15-DHET, and 11,12-DHET, and the antibody immunoreactive with the free form of a specific DHET is an antibody immunoreactive with the free form of a DHET selected from the group comprising 5,6-DHET, 8,9-DHET, 14,15-DHET, and 11,12-DHET.

15. The method as defined in claim 8, wherein said measuring of glucuronidated DHET metabolites includes:
  obtaining a test specimen from said test sample;
  immunoassaying a first sample of the test specimen with an antibody immunoreactive with the glucuronidated form of a specific DHET metabolite;
  immunoassaying a second sample of the test specimen with an antibody immunoreactive with the free form of the specific DHET metabolite; and
  determining the total (free+glucuronidated) amount of the specific DHET metabolite by adding the amount of immunoreactive glucuronidated DHET metabolite in the first sample to the amount of immunoreactive free DHET metabolite in the second sample.

16. The method as defined in claim 15 wherein the antibody immunoreactive with the glucuronidated form of a specific DHET metabolite is an antibody immunoreactive with the glucuronidated form of a DHET metabolite selected from the group comprising 5,6-DHET, 8,9-DHET, 14,15-DHET, and 11,12-DHET, and the antibody immunoreactive with the free form of a specific DHET metabolite is an antibody immunoreactive with the free form of a DHET metabolite selected from the group comprising 5,6-DHET, 8,9-DHET, 14,15-DHET, and 11,12-DHET.

* * * * *